United States Patent [19]
DePalma

[11] Patent Number: 5,832,560
[45] Date of Patent: Nov. 10, 1998

[54] CASTER

[76] Inventor: Richard DePalma, 982 Harrison Ave., Columbus, Ohio 43201

[21] Appl. No.: 800,801

[22] Filed: Feb. 18, 1997

[51] Int. Cl.$^6$ .................................................. B60B 33/00
[52] U.S. Cl. ................................................ 16/30; 36/110
[58] Field of Search .................... 16/30, 35 R, 42 R, 16/43, 31 R; 280/11.19, 11.22, 11.24, 11.3; 36/110, 115, 116

[56] References Cited

U.S. PATENT DOCUMENTS

| | | | |
|---|---|---|---|
| 2,141,099 | 12/1938 | Walters . | |
| 2,762,367 | 9/1956 | Rubin . | |
| 3,744,487 | 7/1973 | Lipson et al. . | |
| 3,802,424 | 4/1974 | Newell . | |
| 3,963,251 | 6/1976 | Miano | 36/115 |
| 3,986,502 | 10/1976 | Gilson . | |
| 4,029,089 | 6/1977 | Mulholland . | |
| 4,059,282 | 11/1977 | Prickett | 16/30 |
| 4,069,543 | 1/1978 | James | 16/42 R |
| 4,177,583 | 12/1979 | Chapman | 36/110 |
| 4,566,208 | 1/1986 | Shaffner | 36/110 |
| 4,567,678 | 2/1986 | Morgan et al. | 36/110 |
| 4,727,660 | 3/1988 | Bernhard | 36/110 |
| 5,388,350 | 2/1995 | Parker, Jr. | 36/115 |
| 5,433,695 | 7/1995 | Drennan . | |
| 5,452,527 | 9/1995 | Gaylord | 36/110 |

*Primary Examiner*—Chuck Mah
*Attorney, Agent, or Firm*—Karen Lee Orzechowski; Nath & Associates

[57] ABSTRACT

A body member is held in place over a foot cast by flexible straps having hook-and-loop faster material. A wheel housing supports a wheel such that in a first orientation of the body member relative to a floor the traction pad is in contact with the floor and the wheel is disposed away from the floor so as to provide traction, and in a second orientation of the body member relative to the floor the traction pad is away from the floor and the wheel is disposed in rolling contact with the floor so as to reduce the traction. The wheel housing can include a toe stop. An adjustable fastening arrangement includes the flexible straps which pass through molded slots of the body member to permit sliding of the flexible strips. An O ring can be used in the adjustable fastening arrangement.

19 Claims, 3 Drawing Sheets

CASTER

FIELD OF THE INVENTION

The present invention is generally directed to walking assistance support devices, and more particularly to walking assistance support devices of the rolling type for individuals with an impaired foot or leg. More specifically, the present invention is directed to a rolling ambulation assistance device having a novel shape that allows for a compact, lightweight design that minimizes the amount of effort necessary to suspend or support an impaired foot or leg during crutch-supported transportation.

BACKGROUND OF THE INVENTION

In general, leg and foot casts are employed to immobilize fractures of bones, sprains or strains in the foot and leg of a patient. When a cast is applied, oftentimes it is inconvenient, heavy, and cumbersome to suspend the impaired foot or leg in the air during crutch-supported transportation. Therefore, it is desirable to be able to convert a cast, shoe, or foot so as to maintain rolling contact between the ground and to ease movement and increase stability during crutch-supported transportation.

The general purpose of the invention is to allow a person wearing a cast, or having an impaired foot, to roll the injured foot along the ground, especially while walking on crutches. The invention is designed to support the impaired foot with a wheel. The apparatus maintains contact with the ground, instead of requiring a person to keep the injured leg and foot suspended in the air. This allows for easier movement, better stability, and less strain on the leg muscles of the impaired foot or leg.

Continued support of an impaired foot or leg is achieved by affixing a rolling mechanism to the toe and bottom surface area of the invention to engage the impaired foot or leg with the ground. In the interest of safety, the rolling mechanism shall be attached at such an angle so that the wheel apparatus is suspended off the ground while the impaired foot or leg is stationary and the bottom of the foot is placed flat on the floor. A non-skid pad on the bottom of the device also keeps the foot from sliding while the impaired foot is resting flat on the ground.

The body of the invention should be constructed of a flexible plastic that fits over a cast, foot, or leg. The body of the invention is attached around the foot by straps bearing hook-and-loop fastener material thereon. At the toe section of the invention is a wheel that allows for rolling of the impaired foot or leg. The wheel should be round and wide to provide stability as it rolls along the ground. The wheel may be made of an in-line skate type polymer material. The wheel may also be designed so that it rolls in only one direction.

Further, the rolling mechanism is positioned on the toe-portion of the invention at such an angle so that it does not touch the ground when the injured foot is stationary and the bottom of the impaired foot is placed flat on the ground. An elastomeric non-skid surface may also be attached to the bottom of the device to improve traction and ensure that the injured foot does not slip or slide while the bottom of the foot is placed flat on the ground.

SUMMARY OF THE INVENTION

An objective of the present invention is to provide walking aid to individuals with a single impaired foot or leg, especially those individuals wearing a cast and needing the use of crutches.

Another objective of this invention is that the device is portable and allows for easy installation and removal.

Another objective of this invention is that it mitigates fatigue and relieves strain on the impaired leg muscles.

A further objective of this invention is that it eases movement and increases stability during crutch-supported movement yet maintains a safe operating mode when the user is stationary.

A further objective of this invention is that it is constructed of light-weight materials to minimize the added load on the impaired leg.

A still further objective of this invention is that it is manufacturable at a relatively inexpensive price.

A still further objective of this invention is that the device is adjustable to accommodate several size and dimension requirements for individual users.

These and other objectives of the present invention are achieved by the walking assistance apparatus of the present invention where a rolling mechanism for maintaining ground contact during transportation is attached to the cast of the impaired foot or leg using light-weight bindings. The invention also provides a safe operating mode for use when the individual is stationary and the bottom of the impaired foot or leg is placed flat on the ground.

The present invention comprises a wheel assembly composed of a body, a wheel, and a wheel housing. Included within the wheel assembly is a wheel that should be round and wide to provide stability as it rolls along the ground. The wheel may also be made of an in-line skate type composed of polymer material. The wheel may also be designed so that it rolls in only one direction. Further, the polymer wheel housing that is attached to the body of the device can be made of an epoxy bond or molded bond. A plastic axle that passes through the wheel housing and through the wheel allows the wheel to spin freely.

The body of the device comprises polymer strips, a molded or adjustable toe stop, molded slots, and hook-and-loop fastener material carried on the straps. The polymer strips of the body cross at the toe and cover the usually exposed toes of the injured person around the top, bottom, and sides of the cast. The interior of the body may be padded to provide better protection against shock. The body is held in place by hook-and-loop fastener material on the straps and by a "toe stop" that can be molded into the body or adjustable to fit the size of the cast and user. The molded or adjustable "toe stop" that holds the wheel housing is attached to the toe and bottom surface of the body and keeps the foot and cast from sliding forward. Fixed to the side strips of the body of the device are molded slots which allows sliding of the straps. Each of the straps can slide through respective molded slots over the top of, as well as behind, the cast, allowing for quick and easy adjustment and securing. Plastic "O" rings allow the straps to be adjusted for tension. Attached to the bottom of the base is a traction pad which is preferably composed of an elastomeric grooved material, and which can be flat or rounded, that provides added traction and prevents the caster from sliding while the traction pad is in contact with the ground.

DETAILED DESCRIPTION OF THE PREFERRED EMBODIMENTS OF THE INVENTION

Figure 1:
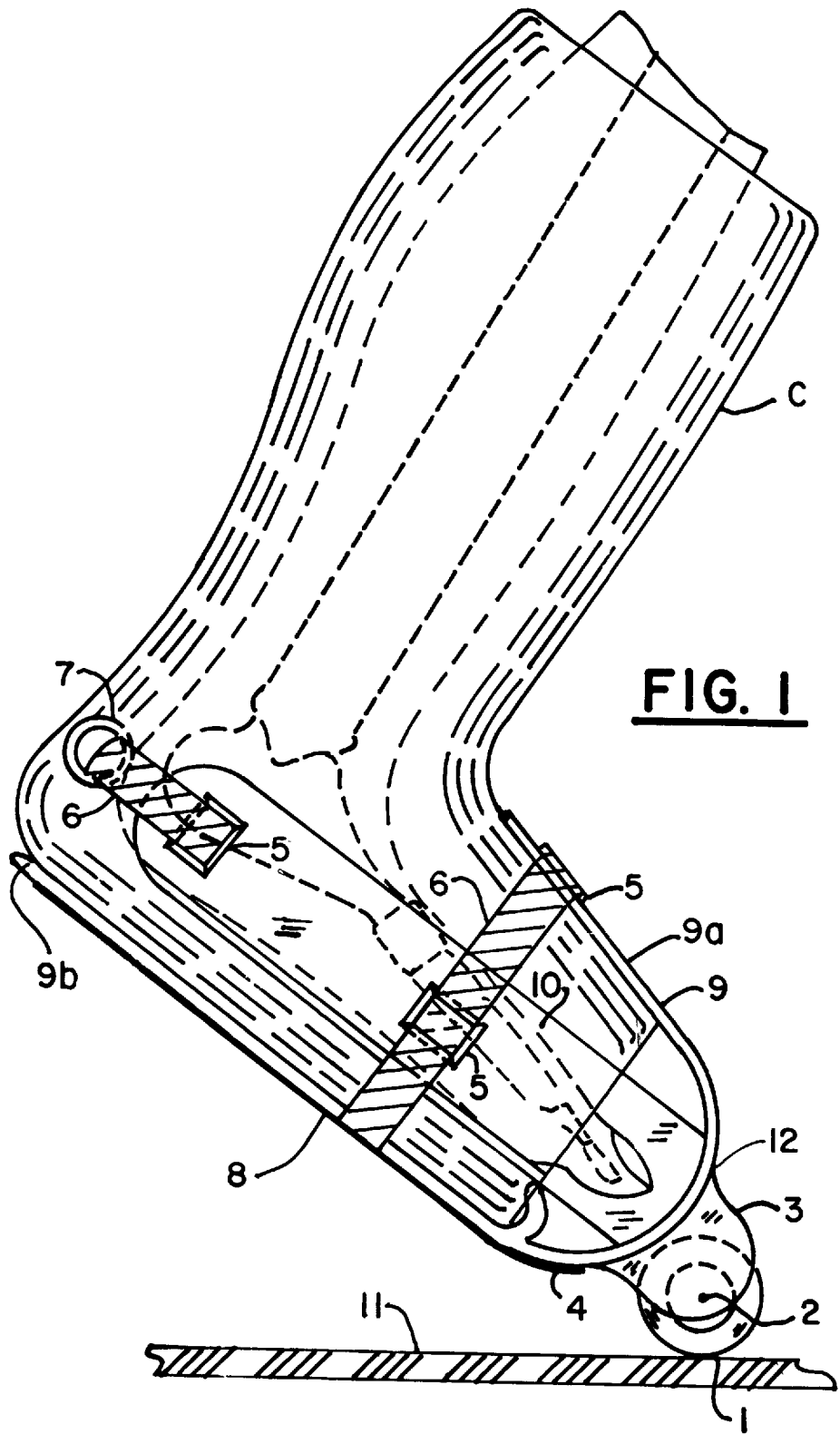
FIG. 1 is a side elevational view of a caster in use applied to a cast, in which a wheel of the caster is in contact with the ground, according to the present invention.

FIG. 1 illustrates a foot cast supported by a caster according to the present invention in rolling engagement with a floor 11. The outline of a foot and lower leg is shown in dashed outline inside a cast C. The caster includes a body piece 9, two side strips 10, and a wheel housing 3.

Figure 2:
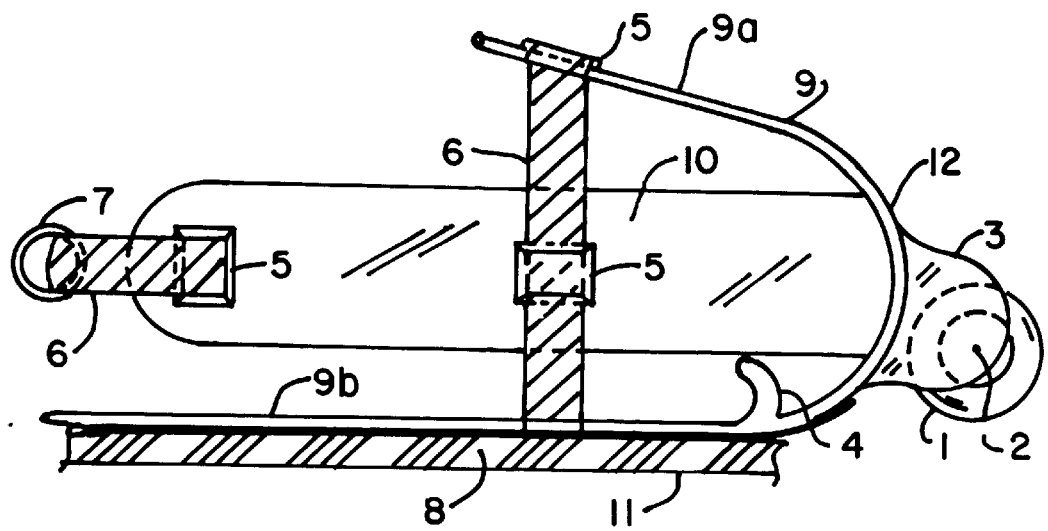
FIG. 2 is a side elevational view of the caster according to the present invention.

A wheel 1 is supported by an axle 2 connected to the wheel housing 3, enabling rotation of the wheel 1. As shown in FIG. 2, the body piece 9 includes a top portion 9a and a bottom portion 9b. The bottom portion 9b carries a traction pad 8.

Figure 6:
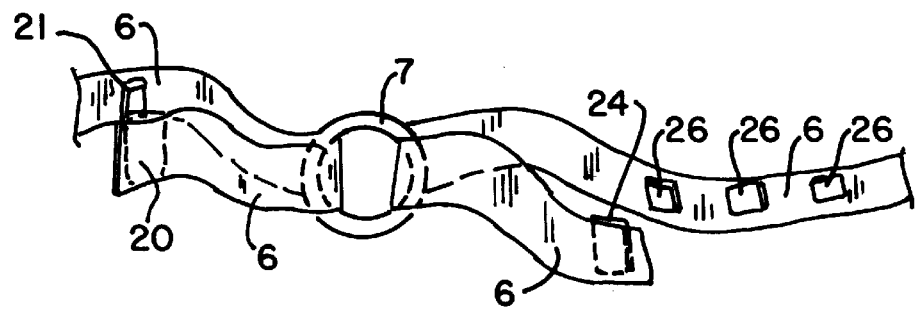
FIG. 6 is a schematic view showing operation of flexible strips of the caster of FIG. 4.

The bottom portion 9b of the body piece 9 includes a toe stop 4 for engagement with the toe portion of a foot cast. Molded slots or guides 5 are provided on the body piece 9 to guide and retain flexible straps 6, so as to permit sliding of the flexible straps 6. Such guides 5 are known in the fastening arts, and are not illustrated in detail herein. The flexible straps 6 are used to secure the body piece 9 to the cast C, and can be fastened as shown in FIG. 6 using hook-and-loop fastener material, for example. The invention encompasses other fastening means as well, including buckles, snaps, slot-and-groove connections, laces, and other types of known connection devices. The guides 5 can be omitted if desired. The flexible straps 6 shown in FIG. 1 as extending from the top portion of body piece 9a to the bottom portion of body piece 9b can likewise be fastened in a similar manner as that shown in FIG. 6, or can be fastened by the other fastening means described hereinabove.

The axle 2 can optionally include a ratcheting or one-way mechanism to permit rolling of the wheel 1 in only a single direction. Such ratcheting mechanisms are well known in the bearing and transmission arts among others, and are not illustrated herein.

While flexible straps 6 are shown as a fastening means, the body piece 9 can alternatively be fastened to the foot cast in other ways as well. For example, the body piece 9 can be permanently affixed to the foot cast by adhesive or cement material, by the cast material itself. Further, rigid strap elements can be used to secure the foot cast inside the body piece 9 using one or more additional components, for example, such as a connecting member which is separably connectable to each rigid strap.

An O ring 7 is shown in FIG. 1 to provide a secure connection of the flexible straps 6. An example of use of the O ring 7 is shown in FIG. 6.

In FIG. 1, the cast C is tilted, for example by bending of the wearer's knee, so that the wheel 1 rolls on the ground. In this position, the traction pad 8 is raised off the floor 11 so that the wheel 1 alone supports the weight of the cast C. In this position, the wearer can move without the necessity of expending the effort to repeatedly raise the cast off the ground.

FIG. 2 is a side elevational view of the caster of the present invention by itself resting on the floor 11. In this position, the wheel 1 is above the floor 11, while the traction pad 8 is in contact with the floor. The elements shown in FIG. 2 are the same as those shown in FIG. 1, and are correspondingly numbered.

Figure 3:
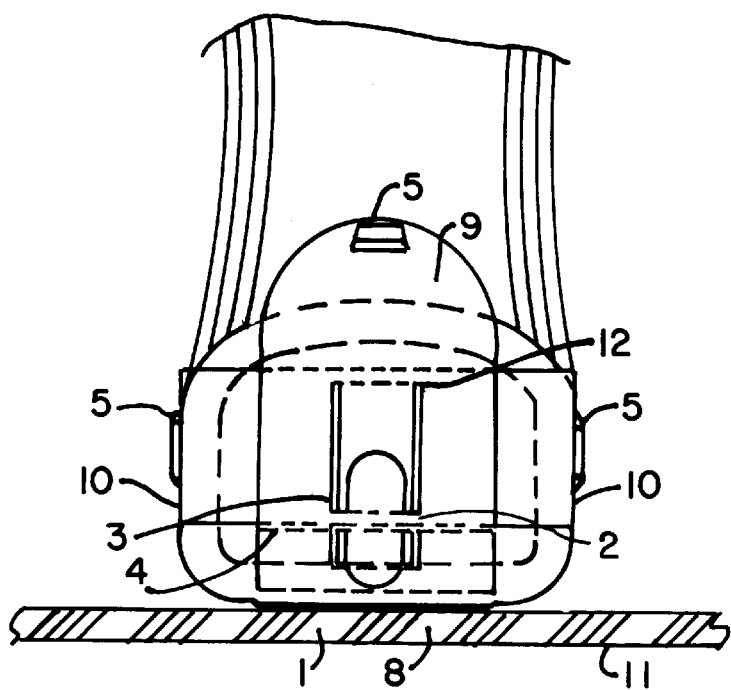
FIG. 3 is a front elevational view of the caster shown in FIG. 1.
Figure 4:
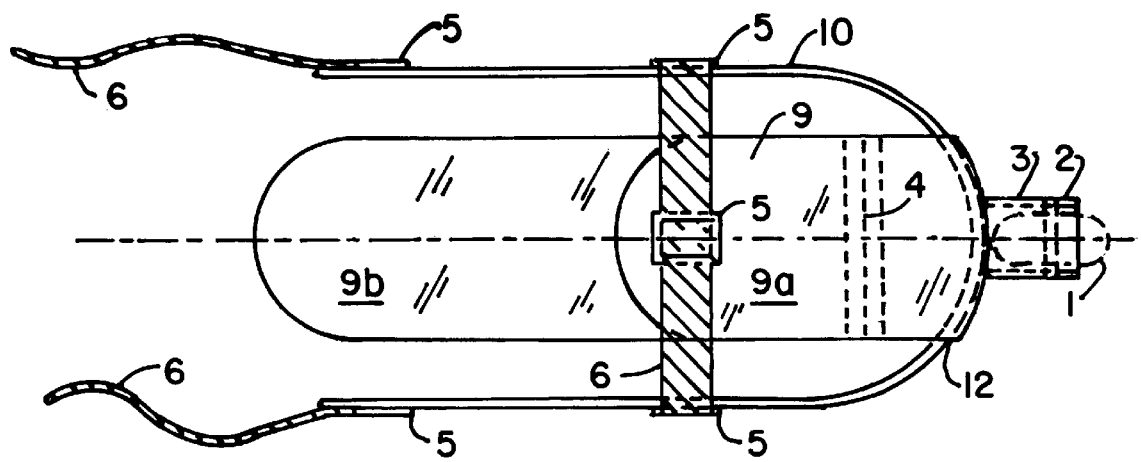
FIG. 4 is a top elevational view of the caster shown in FIG. 2.

FIG. 3 is a front elevational view of the caster shown in FIG. 1, and FIG. 4 is a top elevational view of the caster shown in FIG. 1. In FIG. 4, the pair of flexible straps 6 are shown extending respectively from the side strips 10. The top portion 9a of the body piece 9 is shown overlying the bottom portion 9b of the body piece 9.

Figure 5:
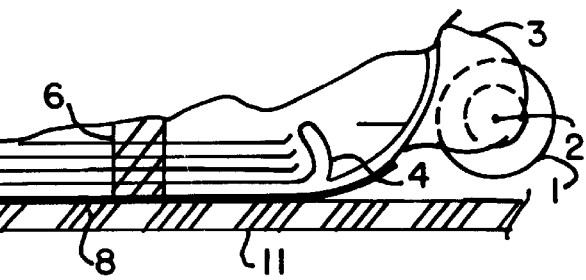
FIG. 5 is a side elevational view of the caster of FIG. 1 with a traction portion of the caster resting on the ground and the wheel raised.

FIG. 5 is a close-up side view of the bottom portion of the caster of FIG. 1 showing the cast C therein, in which the traction portion 8 of the caster rests on the floor 11 with the wheel 1 raised above the floor 11.

FIG. 6 is a schematic view showing features and operation of the flexible straps 6 of the caster of FIG. 4. The flexible straps 6 can carry one or more mating pieces 20, 21 of hook-and-loop fastener material as shown on the left hand side of FIG. 6. The flexible straps 6 can likewise carry a plurality of 26 of hook-and-loop fastener material as shown on the strap 6 on the right hand side of FIG. 6. The flexible straps 6 can be connected or affixed to the body piece 9 by epoxy adhesive, for example, or can be otherwise attached as by riveting, looping through openings formed in the body piece 9, and so on.

Alternatively, one entire surface of each of the flexible straps 6 can be formed of hook-and-loop material. Other arrangements of the hook-and-loop material on the straps are possible, and such alternative arrangements are all contemplated as being within the scope of the present invention. Additionally, while a cast C has been shown, the caster according to the present invention can be applied instead to a shoe or foot.

Accordingly, by the present invention as shown in the drawings and described hereinabove, it is possible to convert a cast, shoe, or foot so as to maintain rolling contact between the ground and to ease movement and increase stability during crutch-supported transportation.

Thus, the person wearing a cast, or having an impaired foot, can roll the injured foot along the ground, especially while walking on crutches. Since the invention supports the impaired foot with a wheel, the apparatus maintains contact with the ground instead of requiring a person to keep the injured leg and foot suspended in the air. This allows for easier movement, better stability, and less strain on the leg muscles of the impaired foot or leg.

While a preferred embodiment of the present invention is described hereinabove with reference to the accompanying drawings, it is not limited to the specific embodiments shown and described, but may be otherwise embodied within the scope of the following claims.

What is claimed is:

1. A caster for use with an impaired foot or leg for attachment to an impaired foot or a foot portion of an impaired leg for minimizing the amount of effort necessary to suspend or support said impaired foot or leg during crutch-assisted transportation over a surface, said caster comprising:

a rolling means, said rolling means comprising a wheel adapted to be affixed to the toe portion of said foot at an angle that enables the wheel to be suspended above the surface when the foot is flat on the surface;

a binding means attached to said rolling means for securing said rolling means to said impaired foot or foot portion of said impaired leg; and a non-skid means for improving traction between the surface and the bottom of said binding means when the impaired foot or leg is stationary and the bottom of the foot is flat on the surface.

2. The caster as defined in claim 1 wherein said binding means comprises a base assembly made up of polymer strips interconnected using Velcro®-like straps for fastening said rolling means to the toe portion of the foot.

3. The caster as defined in claim 1 wherein:

said non-skid means comprises an elastomeric pad attached to the bottom of said binding means.

4. The caster as defined in claim 1 wherein:

said rolling means comprises a round wheel that is wide to provide stability as it rolls along the surface.

5. The caster as defined in claim 1 wherein:

said rolling means comprises a wheel made of polymeric material.

6. The caster as defined in claim 1 wherein:

said rolling means comprises a wheel that rolls in only one direction.

7. The caster as defined in claim 1 wherein:

said binding means comprises a molded or adjustable toe stop containing molded slots; polymer strips attached to said toe stop by means of said molded slots; and Velcro® straps connected to said polymer strips for securing said binding means to said foot.

8. The caster as defined in claim 1 wherein said foot has a toe portion and said binding means further comprises polymer strips, a top portion and a bottom portion, wherein the top portion covers the toe portion of said foot and is secured in place by said polymer strips.

9. The caster as defined in claim 1 wherein:

the binding means comprises a polymeric body wherein the interior of the body is padded to provide better protection against shock.

10. A caster for use over a foot cast comprising:

a body member having an interior portion adapted for receiving the foot cast, said body member having a front portion and bottom portion;

a wheel housing disposed at said front portion of said body member;

a wheel rotatably supported by said wheel housing; and a traction pad connected to said bottom portion of said body member;

said wheel being disposed such that in a first orientation of said body member relative to a surface said traction pad is in contact with the surface and said wheel is disposed away from the surface so as to provide traction, and in a second orientation of said body member relative to the surface said traction pad is disposed away from the surface and said wheel is disposed in rolling contact with the surface so as to reduce the traction.

11. The caster as defined in claim 10 wherein the foot cast has a toe portion and said body member is adapted to receive the foot cast so that the toe portion of said cast is located adjacent said wheel at an angle that enables the wheel to be suspended above the ground when the impaired foot or leg is in the flat on a surface, corresponding to the first orientation.

12. The caster as defined in claim 10, wherein:

said binding means comprises flexible strips including at least one portion carrying a hook-and-loop fastener material, said flexible strips being adjustably connected by the hook-and-loop fastener material.

13. The caster as defined in claim 10 wherein:

said traction pad comprises an elastomeric pad.

14. The caster as defined in claim 10 wherein:

said wheel is wide relative to its diameter, so as to provide rolling stability.

15. The caster as defined in claim 10 wherein:

said wheel is composed of polymer material.

16. The caster as defined in claim 10 further comprising one-way rotation means for permitting rotation of said wheel in only one direction.

17. The caster as defined in claim 10 wherein:

said binding means comprises polymer strips that cross at the toe section and cover the usually exposed toes of the injured person around the top, bottom, and sides of the cast.

18. The caster as defined in claim 10 wherein:

said body member comprises a polymeric body having padding facing the case, to provide shock protection.

19. A caster for use over a shoe or foot, comprising:

a body member adapted for receiving the shoe or foot, said body member having a front portion and bottom portion;

a wheel housing disposed at said front portion of said body member;

a wheel rotatably supported by said wheel housing; and a traction pad connected to said bottom portion of said body member;

said wheel being disposed such that in a first orientation of said body member relative to a surface said traction pad is in contact with the surface and said wheel is disposed away from the surface so as to provide traction, and in a second orientation of said body member relative to the surface said traction pad is away from the surface and said wheel is disposed in rolling contact with the surface so as to reduce the traction.

* * * * *